US009742034B2

(12) United States Patent
Chern et al.

(10) Patent No.: US 9,742,034 B2
(45) Date of Patent: Aug. 22, 2017

(54) CYANO-BENZIMIDAZOLE SALTS FOR ELECTROCHEMICAL CELLS AND METHOD FOR SYNTHESIS THEREOF

(71) Applicant: NATIONAL TAIWAN UNIVERSITY OF SCIENCE AND TECHNOLOGY, Taipei (TW)

(72) Inventors: Yaw-Terng Chern, Taipei (TW); Jyh-Long Jeng, Taipei (TW); Szu-Yuan Chen, Taipei (TW); An-Shing Wei, Taipei (TW); Bing-Joe Hwang, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 203 days.

(21) Appl. No.: 14/139,827

(22) Filed: Dec. 23, 2013

(65) Prior Publication Data
US 2014/0178771 A1  Jun. 26, 2014

(30) Foreign Application Priority Data
Dec. 26, 2012  (TW) .............................. 101149944 A (51) Int. Cl.
*H01M 10/052* (2010.01)
*H01M 10/0567* (2010.01)
(Continued)

(52) U.S. Cl.
CPC ...... *H01M 10/0568* (2013.01); *C07D 235/08* (2013.01); *C07D 235/10* (2013.01);
(Continued)

(58) Field of Classification Search
CPC ......... H01M 10/0568; H01M 10/0525; H01M 10/052; H01M 10/054; H01M 10/0569; C07D 235/08; C07D 235/10
(Continued)

(56) References Cited

U.S. PATENT DOCUMENTS

| 2003/0108800 A1* | 6/2003 | Barbarich ........... H01M 4/5815 429/324 |
| 2006/0068295 A1 | 3/2006 | Xu et al. |

(Continued)

FOREIGN PATENT DOCUMENTS

WO    03/043102 A2    5/2003

OTHER PUBLICATIONS

Heider U, Oesten, Rand Jungnitz, M .. Challenge in manufacturing electrolyte solutions for lithium and lithium ion batteries quality control and minimizing contamination level. J. Power Sources. 1999, 81, 119-122.
(Continued)

*Primary Examiner* — Sean P Cullen
(74) *Attorney, Agent, or Firm* — The PL Law Group, PLLC (57) ABSTRACT

The present invention discloses a new metal cyano-substituted benzimidazolide salt having formula (I) and its preparation. This new cyano-substituted benzimidazole derivatives exhibited excellent thermal stability. The organic salt of the present invention were soluble in an alkyl carbonate solvent, such as propylene carbonate (PC), dimethyl carbonate (DMC) and ethylene carbonate (EC)/DMC cosolvent. The non-aqueous electrolyte prepared by mixing the organic metal salt of the present invention with the alkyl carbonate solvent shows high conductivity and excellent electrochemical stability. The non-aqueous electrolyte is suitable for use in primary or secondary rechargeable batteries.

(Continued)

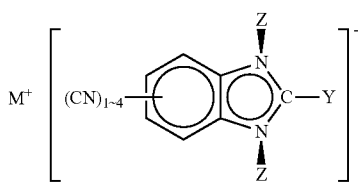

(I)

16 Claims, 9 Drawing Sheets (51) Int. Cl.
- *H01M 10/0568* (2010.01)
- *H01M 10/0569* (2010.01)
- *C07D 235/06* (2006.01)
- *C07D 235/08* (2006.01)
- *H01M 10/054* (2010.01)
- *C07D 235/10* (2006.01)

(52) U.S. Cl.
CPC ....... *H01M 10/052* (2013.01); *H01M 10/054* (2013.01); *H01M 10/0569* (2013.01); *H01M 2300/0025* (2013.01)

(58) Field of Classification Search
USPC ......... 429/338, 188, 200, 341, 342; 548/110
See application file for complete search history.

(56) References Cited

U.S. PATENT DOCUMENTS

| | | | |
|---|---|---|---|
| 2010/0010249 A1 | 1/2010 | Fujinami et al. | |
| 2011/0214895 A1* | 9/2011 | Ihara | H01M 10/056 173/217 |
| 2014/0127556 A1* | 5/2014 | Wang | H01M 10/0568 429/163 |

OTHER PUBLICATIONS

Doron Aurbach. Review of selected electrode-solution interactions which determine the performance of Li and Li ion batteries. J. Power Sources. 2000, 89, 206-218.

Juichi Arai, Akira Matsuo, Takashi Fujisaki and Kazunori Ozawa. A novel high temperature stable lithium salt (Li2B12F12) for lithium ion batteries. J. Power Sources. 2009, 193, 851-854.

V. Aravindan and P. Vickraman. Polyvinylidenefluoride-hexafluoropropylene based nanocomposite polymer electrolytes (NCPE) complexed with LiPF3(CF3CF2)3. European Polymer Journal. 2007 43(12), 5121-5127.

L. Niedzicki, G.Z. Zukowska, M. Bukowska, P. Szczeciiiski, S. Grugeon, S. Laruelle, M. Armand, S. Panero, B. Scrosati, M. Marcinek and W. Wieczorek. New type of imidazole based salts designed specifically for lithium ion batteries. Electrochim. Acta. 2010 55(4), 1450-1454.

LaPointe, R.E., Roof, G.R., Abboud, K.A. and Klosin, J. New Family of Weakly Coordinating Anions. J. Am. Chern. Soc. 2000 122(39), 9560-9561.

X. Sun, H. S. Lee, X. Q. Yang and Borate Compound. J. Electrochem. J. McBreen. A New Additive for Lithium Battery Electrolytes Based on an Alkyl Borate Compound. J. Electrochem. Soc. 2002 149(3), A355-A359.

"Benzimidazole and imidazole lithium salts for battery electrolytes", Journal of Power Sources, vol. 195, Issue 18, Sep. 15, 2010, pp. 6081-6087, Johan Fig. 2 and p. 6068.

Patent Search Report of Application No. 102123719 submitted herein.

Office action from Taiwan Intellectual Property Office in a counterpart Taiwan patent application dated Aug. 19, 2014.

* cited by examiner

IM

BI

MBI

TFBI

5-CNMBI

5-CNTFBI

5-CNPFBI 4,6-DCNMBI

Fig. 1

Li[5-CNMBI(BF$_3$)$_2$]

Li[5-CNTFBI(BF$_3$)$_2$]

Li[4,6-DCNMBI(BF$_3$)$_2$]

Li[5-CNPFBI(BF$_3$)$_2$]

Li[MBI(BF$_3$)$_2$]

Experimental example 1

Experimental example 2

Experimental example 3

Fig. 3A

Experimental example 4

Experimental example 5

Experimental example 6

Fig. 3B

Fig. 4A 4,6-DCNMBI

Fig. 4B

5-CNTFBI

CYANO-BENZIMIDAZOLE SALTS FOR ELECTROCHEMICAL CELLS AND METHOD FOR SYNTHESIS THEREOF

CROSS REFERENCE TO RELATED APPLICATIONS

This application claims benefit under 35 U.S.C. §119 of TW Application No. 101149944, filed Dec. 26, 2012, the contents of which are incorporated by reference as if fully set forth.

FIELD OF THE INVENTION

The present invention relates to an organic salt, which is a metal of a cyano benzimidazole derivative and has thermal and electrochemical stability. The organic salt disclosed in the present invention had excellent thermal and electrochemical stability, and said salt can be formulated with alkyl carbonate as a non-aqueous electrolyte and applied in both primary and secondary electrochemical cells.

BACKGROUND OF THE INVENTION

Lithium ion cells are the fastest-developing storage cells at present, and are broadly used in portable electronic products and household appliances. With the increasing petroleum crisis and global warming problems, it is an urgent need to develop green material and energy-related applications. Among these applications, the development of the electric vehicle is important to decrease petroleum usage in the face of global warming. The lithium cell is the most promising cell that can be used in an electric vehicle, wherein the lithium salt used for portable electronic products is $LiPF_6$. $LiPF_6$ has poor thermal stability, and it tends to decompose into LiF and $PF_5$ when the operating temperature is higher than 60° C. (J. Power Sources 81 (1999) 119; J. Power Sources 89 (2000) 206), wherein $PF_5$ and $LiPF_6$ react with water to produce corrosive HF in the presence of trace water and will cause the corrosion of the current collector layer, deterioration of the solid electrolyte interface (SEI) layer and damage of the electrode material. Currently, lithium cells using $LiPF_6$ cannot be directly applied in electric vehicles because the cells need to be modified so as to repeatedly recharge under a high temperature (>60° C.) for a long time. The most important part of the lithium cell that can be used in electric vehicles is a thermally stable lithium salt, which is the object of the present invention.

The lithium cell primarily consists of graphitic carbon as an anode, lithium transition metal oxide as a cathode and an electrolyte solution having high conductivity. The electrolyte of the lithium ion is formed by dissolving the lithium salt in a non-aqueous solvent, wherein the primary solvents are alkyl carbonates such as ethylene carbonate (EC), dimethyl carbonate (DMC), diethyl carbonate (DEC), ethyl methyl carbonate (EMC) and propylene carbonate (PC).

From the 1990s to the present, $LiPF_6$ has been the dominant commercial lithium salt. $LiPF_6$ has very high conductivity and high solubility in alkyl carbonates, it is electrochemically stable under the operating voltage (<4.2V vs. Li) and can be used at a temperature between −40 to 50, therefore, there is almost no other commercial lithium salt that can replace $LiPF_6$. However, $LiPF_6$ lithium salt cannot be used in a hot environment (>60° C.) because the following reactions will occur when the temperature is higher than 60° C.:

wherein $LiPF_6$ and $PF_5$ react with water to produce corrosive HF in the presence of trace water and result in a decrease in the performance of the cell:

Therefore, because $LiPF_6$ lithium salt cannot be used in a hot environment (>60° C.), there is an urgent need to develop a lithium salt that can be used at high temperatures and is suitable for electric vehicles.

Any lithium salt that can be applied in lithium ion cells must have the following properties: high conductivity, good thermal stability, nontoxicity, safety and electrochemical stability under the potential of a fully charged cell (4.1V vs. Li), but few lithium salts have all these properties. Lithium salts can be classified as inorganic lithium salts and organic lithium salts. Examples of inorganic lithium salts are $LiClO_4$, $LiAsF_6$, $LiPF_6$, $LiBF_4$, $Li_2B_{12}F_{12}$ (referring to J. Power Sources 193 (2009) 851), wherein $LiClO_4$ may explode when it is used, $LiAsF_6$ is highly toxic, $LiBF_4$ has lower ion conductivity and $Li_2B_{12}F_{12}$ also has low ion conductivity due to large anion. These significant disadvantages prevent these lithium salts from being commercialized. Examples of organic lithium salts are $LiN(SO_2CF_3)_2$ (LiTFSI), $LiN(SO_2C_2F_5)_2$(LiBETI), $LiC(SO_2CF_3)_3$, $LiCF_3SO_3$(LiTF), $LiC(SO_2CF_3)_2$ (referring to European Polymer Journal. 43 (2007) 5121). However, these lithium salts cannot be commercialized due to the disadvantage of causing the aluminum collector layer to corrode. Other organic lithium salts such as Lithium tetrakis(haloacyloxy) borates ($Li[B(OCOBX)_4]$), Lithium bis(oxalate)borate (Li-BOB), $LiPF_3(CF_2CF_3)_3$ (LiFAP) (referring to European Polymer Journal. 43 (2007) 5121) cannot be commercialized due to their low ion conductivities.

In the development of high temperature lithium salts, the lithium salt containing heterocyclic anion is main strategy, (referring to Electrochim. Acta 55 (2010) 1450) such as lithium 4,5-dicyanotriazole (LiDCTA). LiDCTA was successfully used in a Polyethylene oxide (PEO) system, but it was not ideal for an EC/DMC system.

One interesting salt is an organic imidazolide lithium salt, lithium bis(trifluoroborane)imidazolide ($Lilm(BF_3)_2$), and this lithium salt has been used in forming lithium ion cells (see J. Am. Chem. Soc., 122, 9560 (2000), J. Electrochem. Soc., 149, A355 (2002)). It has been demonstrated that a cell with an electrolyte containing $Lilm(BF_3)_2$ has comparable performance to a cell containing $LiPF_6$. Unfortunately, a strong base n-butyllithium (n-BuLi) was required to synthesize this type of $Lilm(BF_3)_2$ lithium salt, and a lithium salt made in this way contains impurities that are difficult to remove. As a result, such a lithium salt shows poor overcharge safety and poor performance under high temperature. The anion of lithium salt with good thermal stability is important for the safety of the cells, the thermal stable lithium salt would prevent the cell from smoking and firing even the cell is over-charged. It would therefore be highly desirable to develop a lithium salt with good conductivity, good thermal stability and good electrochemical safety during the charge and re-charge operations of the cells, in order to enhance the safety of the lithium ion cell.

The present invention discloses an organic metal salt having good solubility (>1.0 M) in alkyl carbonates solvents that are commonly used in lithium cells. When dissolving such a salt in alkyl carbonates to prepare a non-aqueous electrolyte, this non-aqueous electrolyte has good conductivity (6.85 mS/cm). The lithium salt of the present invention had excellent thermal stability (i.e. the initial decomposition temperature>200° C.) and oxidation resistant electrochemical stability (i.e. anodic limit>5.0V vs. Li). The present invention also discloses a simple method suitable for preparing a cyano benzimidazole metal salt.

SUMMARY OF THE INVENTION

The present invention discloses an organic metal salt suitable to form electrolytes of primary and secondary electrochemical cells with various non-aqueous solvents, the organic metal salt comprises a structure represented by formula I $$M^+ \left[ (CN)_{1\sim4} \underset{Z}{\overset{Z}{\underset{N}{\bigcirc}}} C{-}Y \right]^- \quad (I)$$

wherein M is one of lithium and sodium,
Z is a Lewis acid, and
Y is one selected from a group consisting of a hydrogen group, an alkyl group, a haloalkyl group, a sulfoalkyl group, a carboalkyl group, a nitroalkyl group, a nitro group, a cyano group, an aldehyde group and a carboxyl group.

Preferably, the Lewis acid is one selected from a group consisting of $BX_3$, $AlX_3$ and $PX_5$, wherein X is a halogen.

Preferably, the Lewis acid is one selected from a group consisting of $BF_3$, $BCl_3$, $BBr_3$, $AlF_3$, $AlCl_3$, $PF_5$, $PCl_5$, $B(OCH_3)_3$, $B(OCF_3)_3$, $B(C_6F_5)_3$, $B(OCH(CF_3)_2)_3$, $B(OC_6F_5)_3$, $B(CF_3)_3$, $B(CF_2CF_3)_3$, $B(OC_6H_4F)_3$, $B(OC_6H_3F_2)_3$, $B(OC_6H_2F_3)_3$, $B(OC_6HF_4)_3$, $B(OCH_2CF_3)_3$, $B(OCH_2C_3F_7)_3$ and $B(CO(CH_3)(CF_3)_2)_3$.

Preferably, Y is one selected from a group consisting of H, $CH_3$, $C_2H_5$, $C_3H_7$, $CF_3$, $CF_2CH_3$, $C_2F_5$, $CH_2CF_2CF_3$, $CF_2CF_2CF_3$, $CF_2CH_2CH_3$, $CF_2CF_2CH_3$, $OCF_3$, $OCH_2CF_3$, $OCF_2CF_3$ and $OCF_2CF_2CF_3$.

According to the present invention, when M is lithium, the organic metal salt is one selected from a group consisting of lithium cyano-1,3-bis(trifluoroborane)benzimidazolide), lithium cyano-1,3-bis(trifluoroborane)-2-methylbenzimidazolide, lithium cyano-1,3-bis(trifluoroborane)-2-trifluoromethylbenzimidazolide, lithium cyano-2-ethyl-1,3-bis(trifluoroborane)benzimidazolide, lithium cyano-1,3-bis(trifluoroborane)-2-pentafluoroethylbenzimidazolide, lithium dicyano-1,3-bis(trifluoroborane)benzimidazolide, lithium dicyano-1,3-bis(trifluoroborane)-2-methylbenzimidazolide, lithium dicyano-1,3-bis(trifluoroborane)-2-trifluoromethylbenzimidazolide, lithium dicyano-2-ethyl-1,3-bis(trifluoroborane)benzimidazolide, lithium dicyano-1,3-bis(trifluoroborane)-2-pentafluoroethylbenzimidazolide, lithium tricyano-1,3-bis(trifluoroborane)benzimidazolide, lithium tricyano-1,3-bis(trifluoroborane)-2-methylbenzimidazolide, lithium tricyano-1,3-bis(trifluoroborane)-2-trifluoromethylbenzimidazolide, lithium tricyano-2-ethyl-1,3-bis(trifluoroborane)benzimidazolide, lithium tetracyano-1,3-bis(trifluoroborane)-2-pentafluoroethylbenzimidazolide, lithium tetracyano-1,3-bis(trifluoroborane)benzimidazolide, lithium tetracyano-1,3-bis(trifluoroborane)-2-methylbenzimidazolide, lithium tetracyano-1,3-bis(trifluoroborane)-2-trifluoromethylbenzimidazolide, lithium tetracyano-2-ethyl-1,3-bis(trifluoroborane)benzimidazolide, lithium tetracyano-1,3-bis(trifluoroborane)-2-pentafluoroethylbenzimidazolide and a combination thereof.

According to the present invention, wherein when M is sodium, the sodium salts are similar to those lithium salts.

The present invention also discloses an electrochemical cell comprising a non-aqueous solvent and an organic metal salt, comprising a structure represented by formula I $$M^+ \left[ (CN)_{1\sim4} \underset{Z}{\overset{Z}{\underset{N}{\bigcirc}}} C{-}Y \right]^- \quad (I)$$

wherein M is one of lithium and sodium,
Z is a Lewis acid and
Y is one selected from a group consisting of a hydrogen group, an alkyl group, a haloalkyl group, a sulfoalkyl group, a carboalkyl group, a nitroalkyl group, a nitro group, a cyano group, an aldehyde group and a carboxyl group.

According to the present invention, the electrochemical cell is one of a primary and a secondary rechargeable cell.

Preferably, the non-aqueous solvent and the organic metal salt form a non-aqueous electrolyte of the electrochemical cell.

The present invention further discloses a method for synthesizing an organic metal salt comprising the steps of reacting a cyano benzimidazole derivative with a metal alkoxide to form an organic salt precursor and reacting the organic salt precursor with a Lewis acid to obtain the organic metal salt.

Other objects, advantages and efficacies of the present invention will be described in detail below taken from the preferred embodiments with reference to the accompanying drawings, in which:

DETAILED DESCRIPTION OF THE PREFERRED EMBODIMENT

The benzimidazole metal salts of the present invention contain a polar cyano group, and therefore these salts have good solubility in polar alkyl carbonates. These salts can be dissolved in a solvent such as propylene carbonate (PC) and dimethyl carbonate (DMC) to make a solubility over 1 M. It is also found that the cyano benzimidazole derivatives had excellent thermal stability, and its initial decomposition temperature is higher than 200° C. The cyano benzimidazole lithium salts had good thermal stability when the cyano benzimidazole derivatives are formed as the anion of lithium salts. The lithium salts of the present invention had over 85% residual rate at 300° C., indicating the good flame resistance of these salts. Because the electron withdrawing cyano group was suspended on the anion of the lithium salt, the dissociation of the salt is easier. The anion after dissociation is relatively stable and thus this cyano benzimidazole salt has high conductivity. Specifically, the benzimidazole metal salts of the present invention had excellent electrochemical stability to oxidation (>5.0 V vs. Li).

The process of preparing the cyano benzimidazole lithium salts of the present invention includes two steps. The first step is to react the relatively weak basic lithium isopropoxide (i-PrOLi) with the cyano benzimidazole derivative in the solvent of anhydrous tetrahydrofuran (THF) to form the lithium salt precursor. The synthesis of the benzimidazole lithium salt precursor was described in U.S. Pat. No. 6,852,446, wherein the first step was to react the strong basic n-butyllithium (n-BuLi) with benzimidazole. However, the strong basic N-BuLi would generate a side reaction with the cyano group and thus it was not suitable for use in the synthesis of the lithium salts precursor containing the cyano benzimidazole derivative. In addition, sodium alkoxide may be adopted to react with the cyano benzimidazole derivative to synthesize the lithium salt precursor, wherein sodium alkoxide may be sodium methoxide, sodium ethoxide, sodium propoxide or sodium butoxide. The second step of the method in the present invention was to react boron trifluoride diethyl etherate ($BF_3(Et_2O)$) with the lithium salt precursor synthesized in the first step state to synthesize the lithium salt, but this step required about 72 hours. To shorten the reaction, boron trifluoride gas ($BF_3$) may also be introduced directly to react with the lithium salt precursor to shorten the reaction time to 24 hours. The present invention discloses a simple method suitable of preparing the lithium salts of the cyano benzimidazole derivatives.

Figure 1:
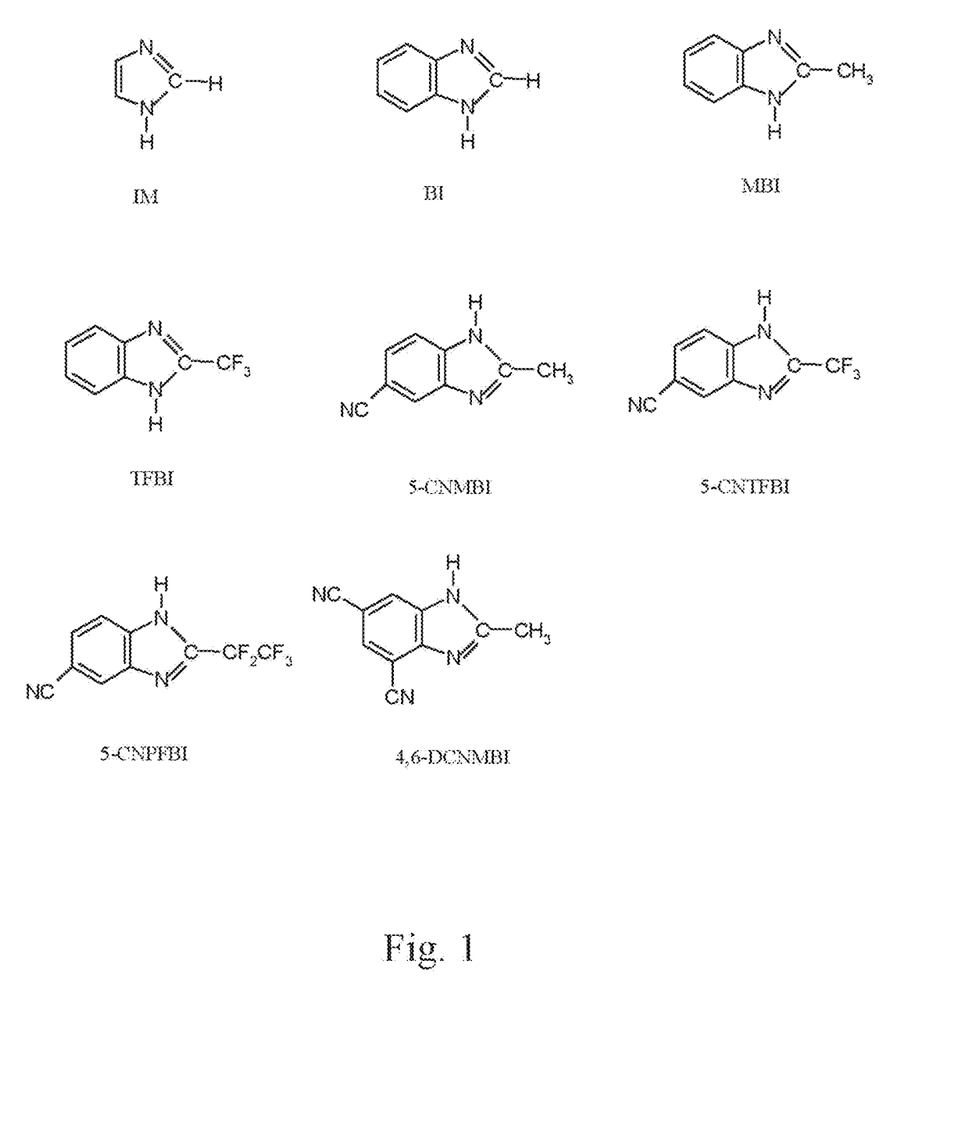
FIG. 1 shows the chemical structures and abbreviations of benzimidazole derivatives.
Figure 2:
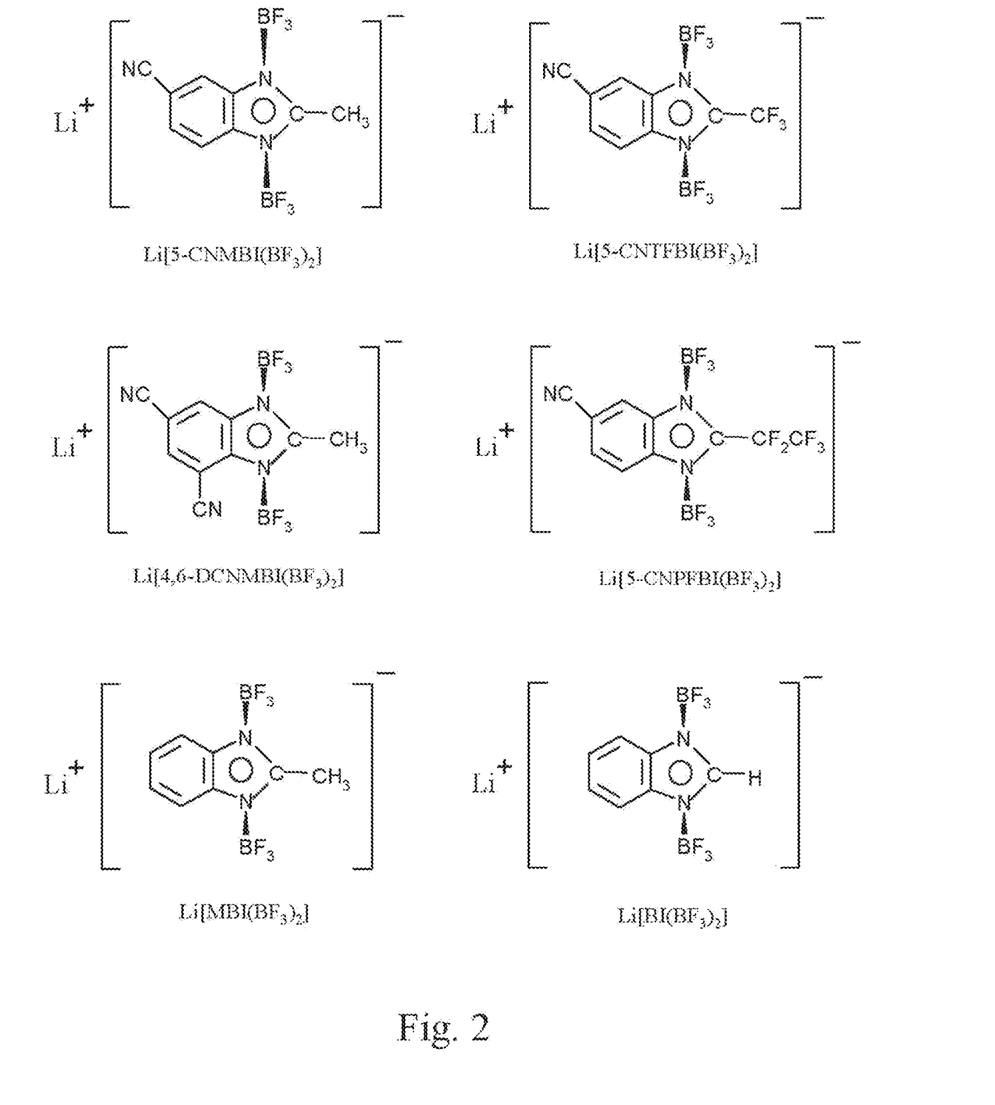
FIG. 2 shows the chemical structures and abbreviations of the lithium salts of the present invention.
Figure 5:
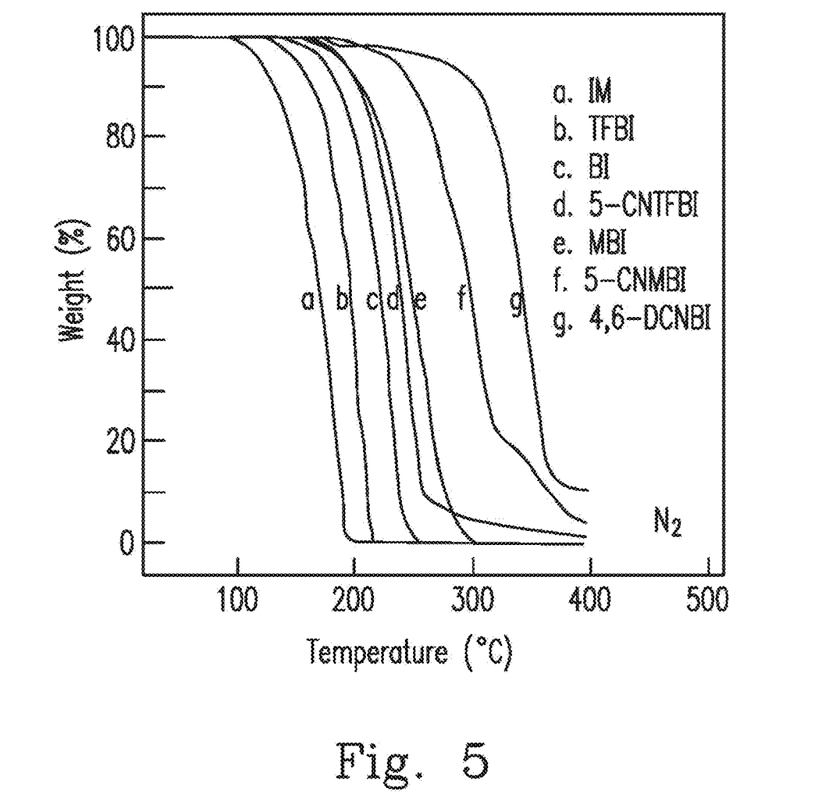
FIG. 5 is shows the thermal stabilities of the benzimidazole derivatives measured in a nitrogen atmosphere at a heating rate of 10° C./min.

The thermal stability of the benzimidazole derivatives was analyzed by using a thermogravimetry analyzer (TGA) in a nitrogen atmosphere at a heating rate of 10° C./min, and the results are shown in FIG. 5. The chemical structures of the benzimidazole derivatives are shown in FIG. 1. In FIG. 5, it can be clearly seen that the thermal stability of the benzimidazole (BI) derivatives were better than that of imidazole (IM). Among the BI derivatives, the cyano benzimidazole derivatives had significantly higher thermal stability. It can be seen that more of the cyano groups on the benzimidazole derivatives had the better thermal stability. All these cyano benzimidazole derivatives had high thermal stability and their initial decomposition temperatures are higher than 200° C. The lithium salts of the present invention were also measured for their thermal stability directly, and it can be seen that these lithium salts had a residual rate of over 85% at 300° C., indicating good flame resistance. The present invention discloses the lithium salts derived from cyano benzimidazole derivatives having excellent thermal stability because the heterocyclic anion of lithium salts can enhance the thermal stability of the lithium salts. When these cyano benzimidazole derivate lithium salts are used in the lithium cells, the safety of the lithium cells is substantially enhanced.

The solubility of the benzimidazole derivative lithium salts are shown in Table 1, where it is noted that the lithium salts containing the polar cyano group show better solubility in PC. For the electrolyte consisting of the lithium salt and the alkyl carbonate, the good solubility of these lithium salts in the alkyl carbonate solvent, are important and necessary.

TABLE 1

The solubility of the benzimidazole lithium salts in PC

| Lithium salts | 0.5M | 0.75M | 1.0M |
|---|---|---|---|
| Li[5-CNPFBI($BF_3$)$_2$] | ○ | ○ | ○ |
| Li[4,6-DCNMBI($BF_3$)$_2$] | ○ | ○ | ○ |
| Li[MBI($BF_3$)$_2$] | ○ | ○ | X |
| Li[BI($BF_3$)$_2$] | ○ | X | X |

Temperature: 25° C.,
○: completely dissolved,
X: partially dissolved

Figure 3A:
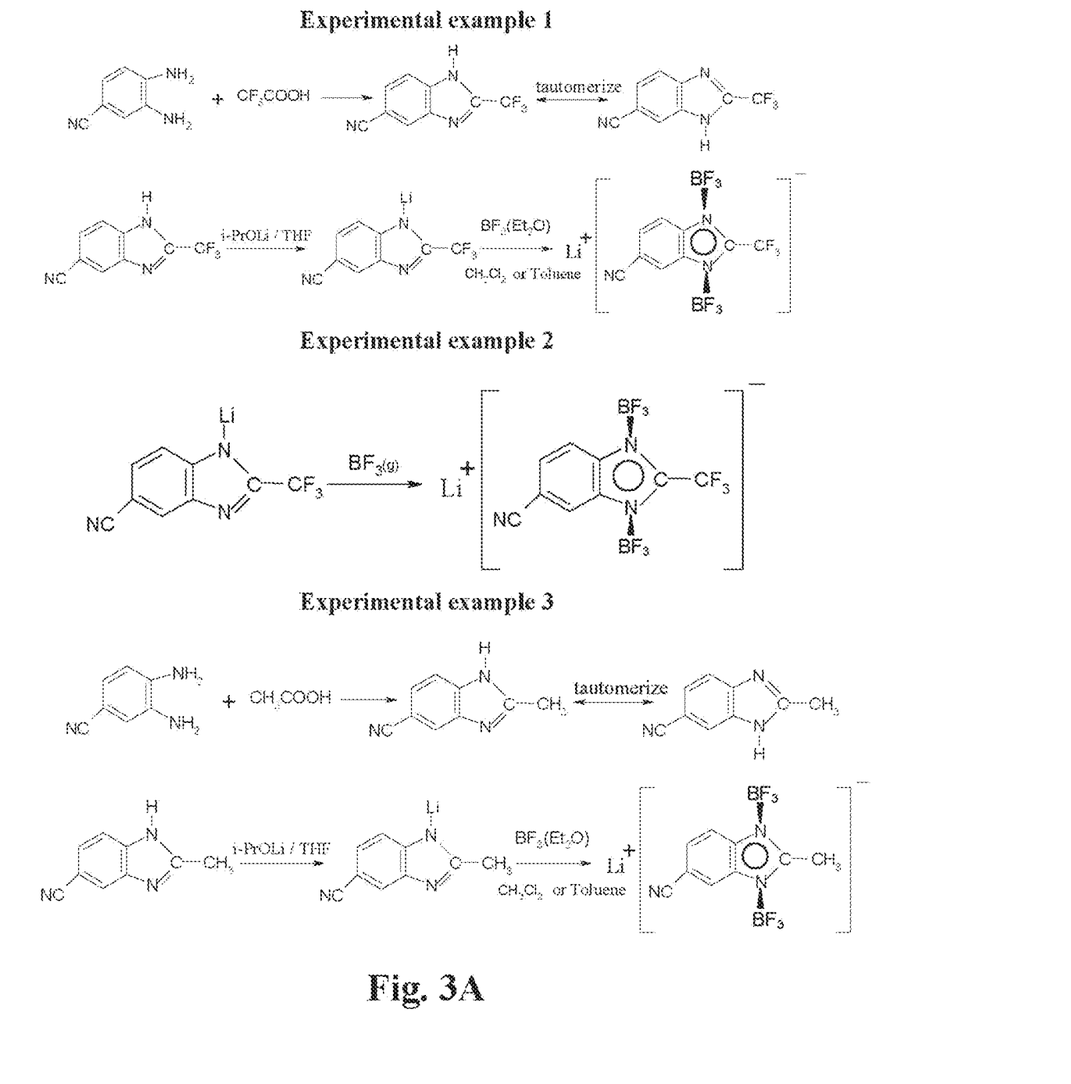
FIG. 3A and FIG. 3B show the processes of synthesizing the lithium salts of the present invention.
Figure 3B:
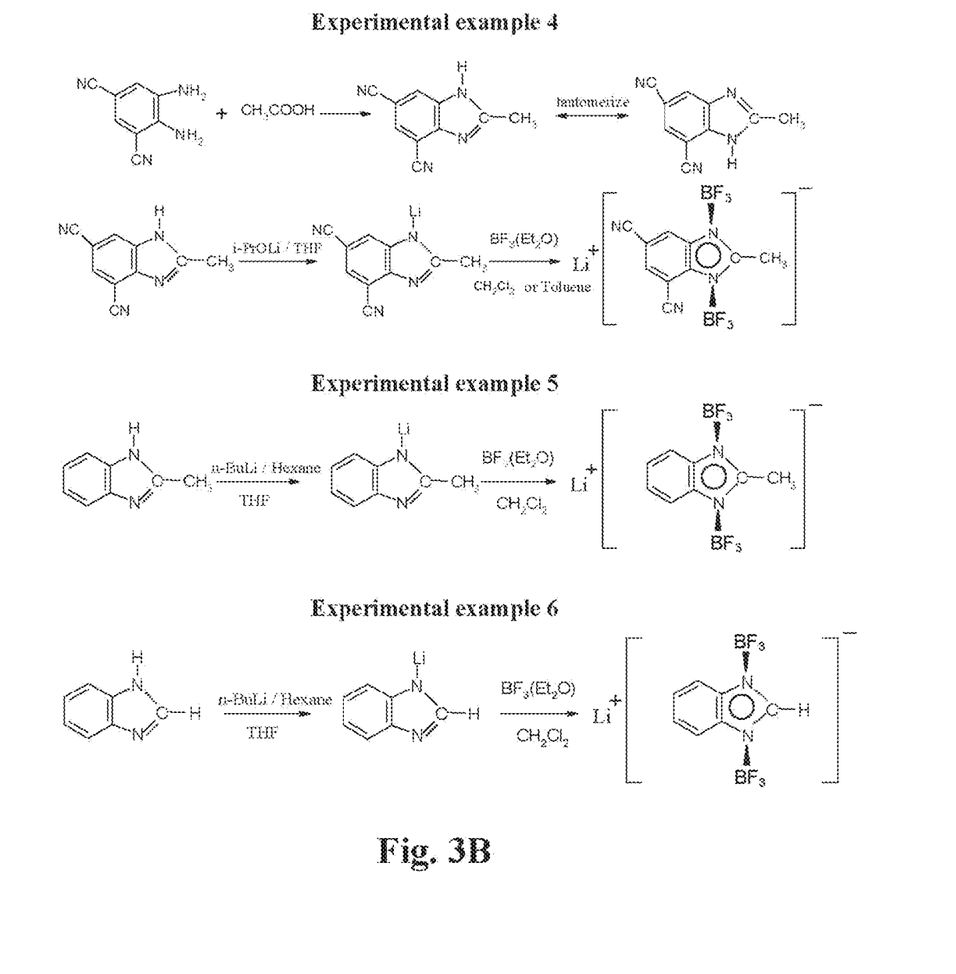
Figure 4A:
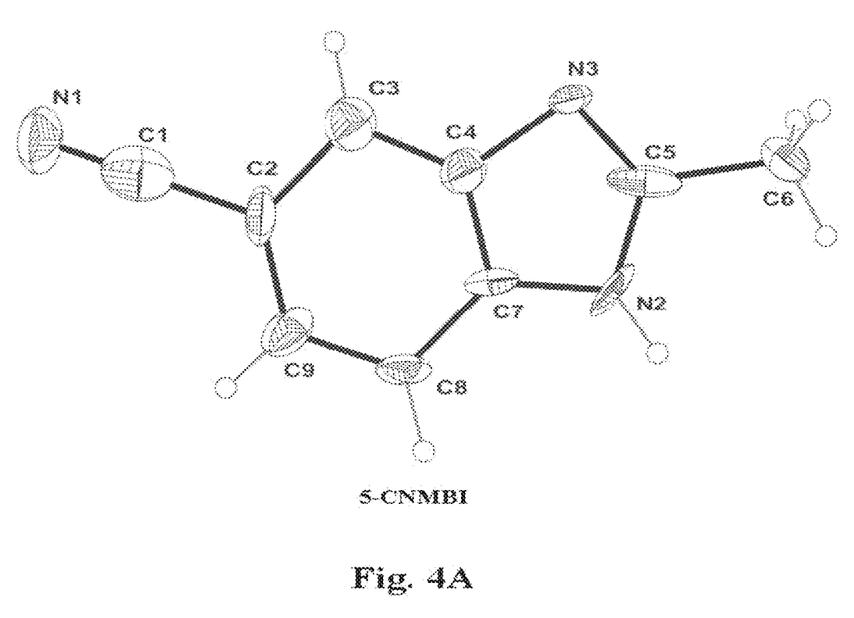
FIGS. 4A, 4B and 4C show the X-ray structures of the benzimidazole derivatives 5-CNMBI, 4,6 DCNMBI and 5-CNTFBI, respectively.
Figure 4B:
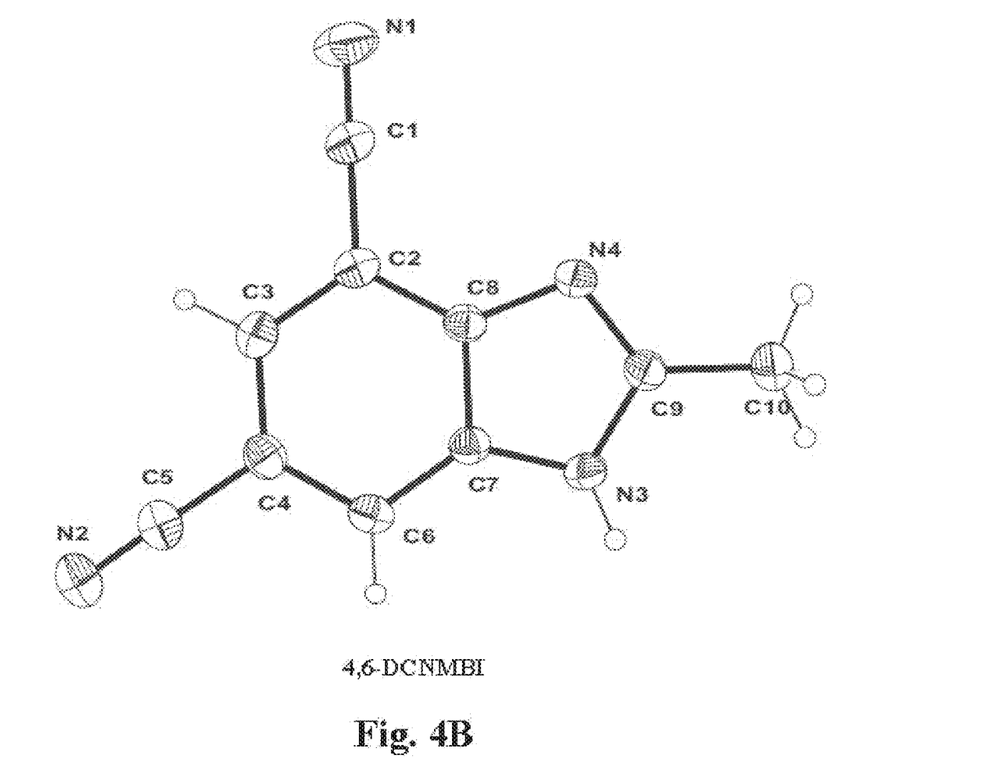
Figure 4C:
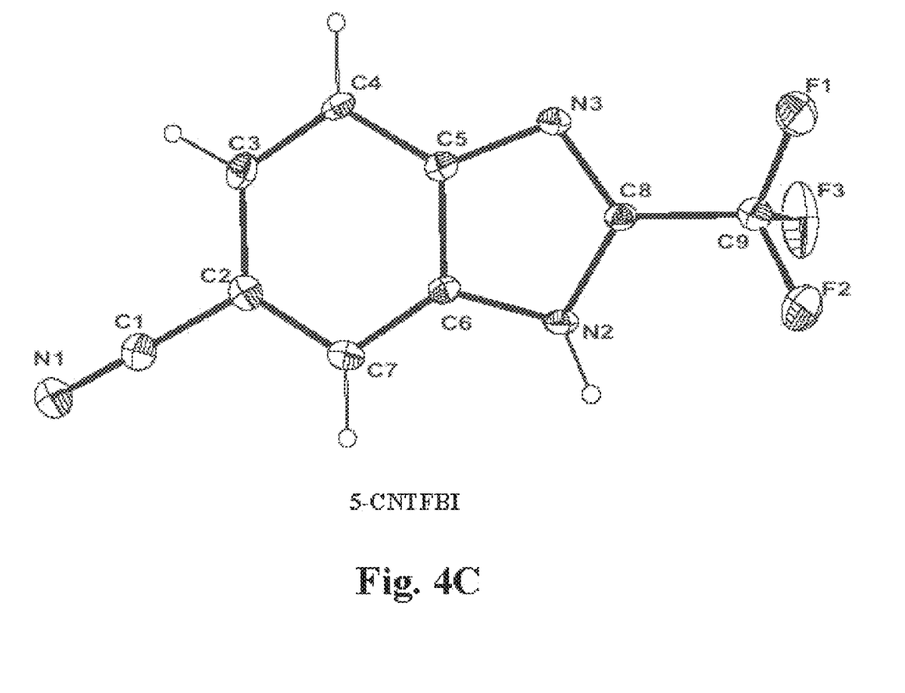

The synthesis of the cyano benzimidazole derivatives are shown in FIG. 3. First, the o-phenylenediamine derivative containing a cyano group was synthesized, and it then directly reacts with acetic acid, trifluoroacetic acid, methanoic acid or pentafluoropropionic acid at reflux. Alternatively, the o-phenylenediamine derivative may be cyclized with acetic anhydride or trifluoroacetic anhydride in the presence of an acidic catalyst to become a benzimidazole derivative. This acidic catalyst may be polyphosphoric acid, P2O5, p-toluenesulfonic acid or hydrochloric acid. Since the method for synthesizing the cyano benzimidazole derivative is complicated and difficult, there have been no reports for synthesis of cyano benzimidazole derivatives. The present invention is the first study for synthesis of the novel cyano benzimidazole derivatives, and the X-ray structures of these cyano benzimidazole derivatives are shown in FIGS. 4A to 4C.

The conductivity of the cyano benzimidazole derivative lithium salts of the present invention were measured at 25. 5-CNTFBI lithium salt dissolved in EC/DMC (with volume ratio of 1/1) as 0.5M lithium salt had the high conductivity 6.85 mS/cm, and 4,6-DCNMBI lithium salt dissolved in EC/DMC (with volume ratio of 1/1) as 0.75M lithium salt had conductivity 6.22 mS/cm. In addition, $LiPF_6$ salt dissolved in EC/DMC (with volume ratio of 1/1) as 0.5M lithium salt had conductivity 8.5 mS/cm. These results show that this new type of lithium salt has sufficiently high conductivity and is suitable for use in the lithium cell.

Figure 6:
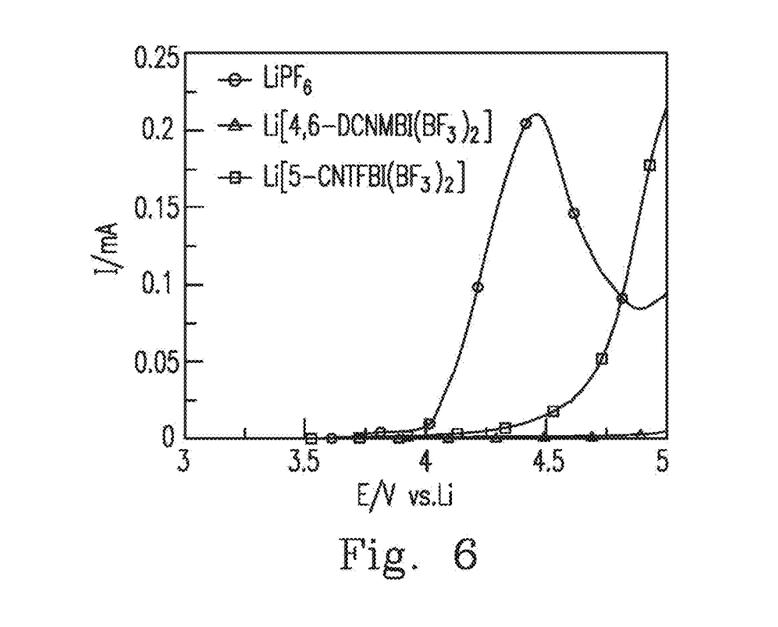
FIG. 6 shows electrochemical stability of the 0.5M lithium salts dissolved in EC/DMC (1/1 v/v).

The electrochemical stability of the cyano benzimidazole derivative lithium salts of the present invention are shown in FIG. 6. The electrochemical stability of the cyano benzimidazole derivative lithium salts of the present invention are clearly much better than that of $LiPF_6$ (anodic limit 4.05V), wherein the anodic limit of 5-CNTFBI is 4.6V. When the cyano group increases, the resistance to oxidation is better, i.e. the highest anodic limit of 4,6-DCNBI over 5.0V, and thus these novel lithium salts are suitable for use in the lithium cell.

Figure 7:
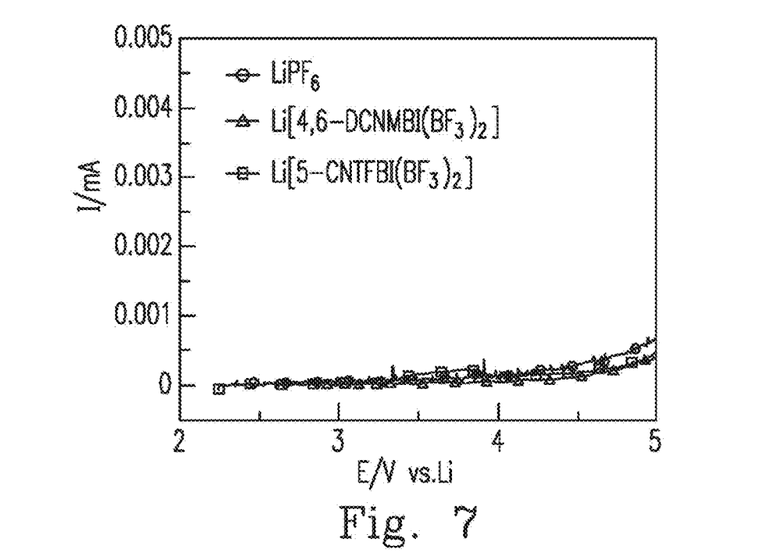
FIG. 7 shows corrosiveness of the 0.5M cyano benzimidazole lithium salts dissolved in EC/DMC (1/1 v/v) against Al collectors.

Corrosiveness of the cyano benzimidazole lithium salts against Al collectors are shown in FIG. 7. All the tested lithium salts do not any corrode to Al collectors before 5.0 V. The electrolytes prepared with these lithium salts is enough for all kinds of commercially used cathodes.

Experiments:

All the electrical property measurements were completed in a strictly air- and moisture-free glove box filled with pure Ar gas. $BF_3(Et_2O)$ was obtained from Alfa Aesar. Nuclear magnetic resonance (NMR) spectrum was analyzed using a BRUKER Avance 500 NMR spectrometer, and the chemical shift is referenced to $Si(CH_3)_4$ ($\delta$=0 vs. $^1H$ NMR). The negative and positive-ion electrospray mass spectra (ESI) was analyzed using a Finnigan LCQ ESI mass spectrometer. The single crystal diffraction of the compound was analyzed using a Nonius Kappa CCD single crystal diffraction meter, and the thermal stability measurements were measured by using a TA TGA Q500 thermogravimetric analyzer in a nitrogen atmosphere at a heating rate of 10° C./min.

The cyclic voltammetry (CV) and conductivity were measured using a Solartron 1480 multichannel potentiostat. The electrochemical stability of the lithium salts was measured in a Li/electrolyte/stainless steel electrochemical system, and the Al collector corrosion resistance of the lithium salts was measured in a Li/electrolyte/Al electrochemical system. The electrolyte is 0.5M Li[5-CNTFBI(BF$_3$)$_2$] dissolved in EC/DMC (1/1 volume ratio) solvent and was scanned under 20° C. at a scanning rate of 5 mV/sec.

Experimental Example 1. Synthesis of Lithium 5-cyano-2-trifluoromethyl-1,3-bis(trifluoroborane) benzimidazolide (Li[5-CNTFBI(BF$_3$)$_2$])

Synthesis of 4-amino-3-nitrobenzonitrile: 20 g (92.2 mmol) of 4-bromo-2-nitroaniline and 20.8 g of cuprous cyanide were dissolved in 150 ml of N,N-dimethylformamide (DMF) to reflux in a nitrogen atmosphere for 20 hours. The mixture was cooled and poured into ice water, extracted with ethyl acetate, concentrated, recrystallized and dried to obtain 5.88 g of product (yield 39.1%) having a melting point of 160~162° C.

Synthesis of 3,4-diaminobenzonitrile: 10 g (61.3 mmol) of 4-amino-3-nitrobenzonitrile and 50 g of stannous chloride were dissolved in 200 ml ethanol to reflux in a nitrogen atmosphere for 6 hours. The mixture was then poured into water and alkalinized to pH 8~9. The filtrate was collected by filtration, and washed with water twice. After being dried, the filtrate was extracted with ethyl acetate, concentrated and recrystallized to obtain 5.75 g of product (yield 70.4%) having a melting point of 144~146° C.

Synthesis of 5-cyano-2-trifluoromethylbenzimidazole (5-CNTFBI): 5.0 g (37.56 mmol) of 3,4-diaminobenzonitrile was dissolved in 20 ml of trifluoroacetic acid to reflux in a nitrogen atmosphere for 10 hours. The mixture was then poured into water and filtered to collect the filtrate. The filtrate was washed with water 3 times and dried to obtain 4.91 g of product (yield 62.0%) having a melting point of 194~196° C.

1H NMR (500 MHz, DMSO-d6) δ: 7.78 (d, J=8.5 Hz, 1H), 7.90 (d, J=8.5 Hz, 1H), 8.37 (s, 1H) ppm.

MS(EI): m/z 211.2 (M+, 100).
The crystal data of the X-ray structure (FIG. 4C): C9H4F3N3, colorless, sheet crystal, 0.52×0.10×0.04 mm3, monoclinic, a=7.7686(7) Å, b=12.7926(11) Å, c=9.6568(8) Å, α=90°, β=112.332(6)°, γ=90°, Dc=1.580 Mg/m$^3$ with Z=4, V=887.72(13) Å3, F(000)=424, finial R indices: R1=0.1331, wR2=0.3894.

Synthesis of Lithium 5-cyano-2-trifluoromethyl benzimidazolate (Li(5-CNTFBI)): 5 g of 5-cyano-2-trifluoromethyl benzimidazole was dissolved in 100 ml of THF, and 15 ml of 3M lithium isopropoxide (i-ProLi) in the THF solution was then added to reflux for 24 hours. The mixture was then poured into hexane, filtered to collect the filtrate and the filtrate was dried to obtain 4.5 g of product (yield 87%).

Synthesis of Lithium 5-cyano-2-trifluoromethyl-1,3-bis (trifluoroborane)benzimidazolide (Li[5-CNTFBI(BF$_3$)$_2$]): 4.5 g of Li(5-CNTFBI) was suspended in 60 ml of dichloromethane, and 10 ml of boron trifluoride diethyl etherate (BF$_3$(Et$_2$O)) was added to reflux for 72 hours. Then, the filtrate was collected and dried to obtain 6.25 g of product (yield 86%).

1H NMR (500 MHz, DMSO-d$_6$) δ: 7.75 (d, J=8.5 Hz, 1H), 7.87 (d, J=8.5 Hz, 1H), 8.34 (s, 1H) ppm.

Negative ESI MS, C$_9$H$_3$B$_2$F$_9$N$_3$ calculation value 346, measured m/z 346[(M-Li)]$^-$.

Experimental Example 2. Synthesis of Lithium 5-cyano-2-trifluoromethyl-1,3-bis(trifluoroborane) benzimidazolide (Li[5-CNTFBI(BF$_2$)$_2$])

Synthesis of Li[5-CNTFBI(BF$_3$)$_2$]: 4.5 g of Li(5-CNTFBI) was suspended in 60 ml of dichloromethane, and BF$_3$ (g) was introduced directly thereinto to reflux for 24 hours. The filtrate was then collected to obtain 6.02 g of product (yield 83%).

Experimental Example 3. Synthesis of Lithium 5-cyano-2-methyl-1,3-bis(trifluoroborane)benzimidazolide Synthesis of 5-cyano-2-methylbenzimidazole (5-CN-MBI): 5.0 g (37.56 mmol) of 3,4-diamino benzonitrile was dissolved in 50 ml of acetic acid to reflux in a nitrogen atmosphere for 12 hours. The mixture was then poured into water, filtered to collect the filtrate and the filtrate was dried to obtain 3.76 g of product (yield 63.7%) having a melting point of 238~240° C.

1H NMR (500 MHz, DMSO-d6) δ: 2.54 (s, 3H), 7.55 (m, 2H), 8.00 (s, 1H), 12.75 (s, 1H) ppm.

MS(EI): m/z 157 (M+, 100).

Crystal data of X-ray structure (FIG. 4A): C$_9$H$_7$N$_3$, colorless sheet crystal, 0.72×0.35×0.02 mm$^3$, orthorhombic, a=9.886(9) Å, b=13.350(13) Å, c=6.186(5) Å, α=β=γ=90°, Dc=1.279 Mg/m$^3$ with Z=4, V=816.3(13) Å3, F(000)=328, finial R indices: R1=0.1357, wR2=0.2184.

Synthesis of lithium 5-cyano-2-methylbenzimidazolate (Li(5-CNMBI)): 5 g of 5-CNMBI was dissolved in 100 ml of THF, and 15 ml of 5M lithium isopropoxide in the THF was added to reflux for 24 hours. The mixture was then poured into hexane and filtered to collect the filtrate. The filtrate was dried to obtain 4.26 g of product (yield 82.0%).

Synthesis of lithium 5-cyano-2-methyl-1,3-bis(trifluoroborane)benzimidazolide (Li[5-CNMBI(BF$_3$)$_2$]): 5 g of Li (5-CNMBI) was suspended in 60 ml of dichloromethane and 10 ml of BF$_3$(Et$_2$O) was added to reflux for 72 hours. The mixture was then filtered to collect the filtrate. The filtrate was dried to obtain 7.75 g of product (yield 84.5%).

$^1$H NMR (500 MHz, DMSO-d$_6$) δ: 2.56 (s, 3H), 7.54 (m, 2H), 8.02 (s, 1H) ppm.

Negative ESI MS, C$_9$H$_6$B$_2$F$_6$N$_3$ calculation value 292, measured m/z 292[(M-Li)]$^-$.

Experimental Example 4. Synthesis of Lithium 4,6-Dicyano-1,3-bis(trifluoroborane)-2-methylbenzimidazole (Li[4,6-DCNTFBI(BF$_3$)$_2$])

Synthesis of 2-amino-3,5-dibromoaniline: 10 g (33.8 mmol) of 2,4-dibromo-6-nitroaniline and 35 g of stannous chloride were dissolved in 100 ml of ethanol to reflux in a nitrogen atmosphere for 6 hours. The mixture was then poured into water and alkalinized to pH 8~9. The filtrate was collected by filtration, and washed with water twice. After being dried, the filtrate was extracted with ethyl acetate, concentrated and recrystallized to obtain 5.64 g of product (yield 62.8%) having a melting point of 78~80° C.

Synthesis of 2-amino-3,5-dicyanoaniline: 20 g (75.2 mmol) of 2-amino-3,5-dibromoaniline and 17 g of cuprous cyanide were dissolved in 200 ml of DMF to reflux in a nitrogen atmosphere for 20 hours. The mixture was cooled and poured into ice water, extracted with ethyl acetate, concentrated, recrystallized and dried to obtain 4.08 g of product (yield 35.0%) having a melting point of 240~244° C.

Synthesis of 4,6-dicyano-2-methylbenzimidazole (4,6-DCNMBI): 2.0 g (12.66 mmol) of 2-amino-3,5-dicyanoaniline was dissolved in 20 ml of acetic acid to reflux in a nitrogen atmosphere for 12 hours. The filtrate was collected and dried to obtain 1.39 g of product (yield 60.3%) having a melting point of 290~292° C.

1H NMR (500 MHz, DMSO-d6) δ: 2.62 (s, 3H), 8.16 (s, 1H), 8.33 (s, 1H) ppm.

MS(EI): m/z 182 (M+, 100).

Crystal data of the X-ray structure (FIG. 4B): C10H6N4, colorless acicular crystal, 0.52×0.33×0.15 mm$^3$, monoclinic a=8.6691(4) Å, b=11.3559(5) Å, c=9.2600(4) Å, α=90°, β=93.054(2)°, γ=90°, Dc=1.329 Mg/m$^3$ with Z=4, V=910.31 (7) Å3, F(000)=376, finial R indices: R1=0.042, wR2=0.1126.

Synthesis of lithium 4,6-dicyano-2-methyl benzimidazolate (Li(4,6-DCNMBI)): 2.5 g of 4,6-DCNMBI was dissolved in 20 ml of THF, and 6.0 ml of 3M lithium isopropoxide (i-ProLi) in the THF solution was then added to reflux for 24 hours. The mixture was then poured into hexane, filtered to collect the filtrate and the filtrate was dried to obtain 2.00 g of product (yield 81.3%).

Synthesis of lithium 4,6-dicyano-1,3-bis(trifluoroborane)-2-methylbenzimidazolide (Li[4,6-DCNTFBI(BF$_3$)$_2$]): 2.00 g of Li(4,6-DCNMBI) was suspended in 25 ml of dichloromethane, and 3.5 ml of BF$_3$(Et$_2$O) was added to reflux for 72 hours. The filtrate was then collected to obtain 2.70 g of product (yield 78.3%).

$^1$H NMR (500 MHz, DMSO-d$_6$) δ: 2.62 (s, 3H), 8.20 (s, 1H), 8.36 (s, 1H) ppm.

Negative ESI MS, C$_{10}$H$_5$B$_2$F$_6$N$_4$ calculation value 317, measured m/z 317[(M-Li)]$^-$.

Experimental Example 5. Synthesis of Lithium 2-methyl-1,3-bis(trifluoroborane)benzimidazolide Synthesis of lithium 2-methylbenzimidazolate (Li(MBI)): 5.0 g of 2-methylbenzimidazole was dissolved in 30 ml of THF solution. The solution was cooled to 0° C., and 15 ml of 2.8 M n-BuLi in a hexane solution was added. After 10 minutes of the reaction, the mixture began to precipitate some powder and was allowed to reflux for 24 hours. The mixture was filtered to collect the filtrate, the filtrate was washed with anhydrous hexane three times and dried to obtain 4.45 g of product (yield 85%).

Synthesis of lithium 2-methyl-1,3-bis(trifluoroborane) benzimidazolide (Li[MBI(BF$_3$)$_2$]): 5 g of Li (MBI) was suspended in 60 ml of dichloromethane, and 11 ml of BF$_3$(Et$_2$O) was added to reflux for 3 days. The mixture was then filtered to collect the filtrate, the filtrate was dried in a vacuum to obtain 8.84 g of product (yield 90%).

Experimental Example 6. Synthesis of Lithium 1,3-bis(trifluoroborane)benzimidazolide Synthesis of lithium benzimidazolate (Li(BI)): 5.0 g of benzimidazole was dissolved in 30 ml of THF solution. The solution was cooled to 0° C., and 15 ml of 2.8M n-BuLi in a hexane solution was added. After 10 minutes of the reaction, the mixture began to precipitate some powder and was allowed to reflux for 24 hours. The mixture was filtered to collect the filtrate, the filtrate is washed with anhydrous hexane three times and dried to obtain 4.72 g of product (yield 89.9%).

Synthesis of lithium 1,3-bis(trifluoroborane)benzimidazolide (Li[BI(BF$_3$)$_2$]): 5 g of Li(BI) was suspended in 60 ml of dichloromethane, and 11 ml of BF$_3$(Et$_2$O) was added to reflux for 3 days. The mixture was then filtered to collect the filtrate, the filtrate was dried in a vacuum to obtain 9.5 g of product (yield 90.8%).

What is claimed is:

1. An organic metal salt, comprising a structure represented by formula I $$M^+ \left[ (CN)_{1-4} \underset{\underset{Z}{\uparrow}}{\overset{\overset{Z}{\downarrow}}{\text{benzimidazole-C—Y}}} \right]^-$$ (I)

wherein

M is lithium;

Z is a Lewis acid; and

Y is one selected from a group consisting of an alkyl group, a sulfoalkyl group, a carboalkyl group, a nitroalkyl group, a nitro group, an aldehyde group, a carboxyl group, OCF$_3$, OCH$_2$CF$_3$, OCF$_2$CF$_3$ and OCF$_2$CF$_2$CF$_3$.

2. An organic metal salt as claimed in claim 1, wherein the Lewis acid is one selected from a group consisting of BX$_3$, AlX$_3$ and PX$_5$, wherein X is a halogen.

3. An organic metal salt as claimed in claim 1, wherein the Lewis acid is one selected from a group consisting of BF$_3$, BCl$_3$, BBr$_3$, AlF$_3$, AlCl$_3$, PF$_5$, PCl$_5$, B(OCH$_3$)$_3$, B(OCF$_3$)$_3$, B(C$_6$F$_5$)$_3$, B(OCH(CF$_3$)$_2$)$_3$, B(OC$_6$F$_5$)$_3$, B(CF$_3$)$_3$, B(CF$_2$CF$_3$)$_3$, B(OC$_6$H$_4$F)$_3$, B(OC$_6$H$_3$F$_2$)$_3$, B(OC$_6$H$_2$F$_3$)$_3$, B(OC$_6$HF$_4$)$_3$, B(OCH$_2$CF$_3$)$_3$, B(OCH$_2$C$_3$F$_7$)$_3$ and B(CO(CH$_3$)(CF$_3$)$_2$)$_3$.

4. An organic metal salt as claimed in claim 1, wherein the alkyl group is one selected from a group consisting of CH$_3$, C$_2$H$_5$ and C$_3$H$_7$.

5. An organic metal salt as claimed in claim 1, wherein the organic metal salt is one selected from a group consisting of lithium cyano-1,3-bis(trifluoroborane)-2-methylbenzimidazolide, lithium dicyano-1,3-bis(trifluoroborane)-2-methylbenzimidazolide, lithium tricyano-1,3-bis(trifluoroborane)-2-methylbenzimidazolide, lithium tetracyano-1,3-bis(trifluoroborane)-2-methylbenzimidazolide, and a combination thereof.

6. A method for synthesizing an organic metal salt, the method comprising:

reacting a cyano benzimidazole derivative with a metal alkoxide to form an organic salt precursor; and reacting the organic salt precursor with a Lewis acid to obtain the organic metal salt, wherein the organic metal salt comprises a structure represented by formula I:

(I)

wherein
M is lithium;
Z is a Lewis acid; and
Y is one selected from a group consisting of an alkyl group, a sulfoalkyl group, a carboalkyl group, a nitroalkyl group, a nitro group, an aldehyde group, a carboxyl group, $OCF_3$, $OCH_2CF_3$, $OCF_2CF_3$ and $OCF_2CF_2CF_3$.

7. A method as claimed in claim 6, wherein the metal alkoxide is one of lithium alkoxide (LiOR) and sodium alkoxide (NaOR), wherein R is one selected from a group consisting of a methyl group, an ethyl group, a propyl group and a butyl group.

8. A method as claimed in claim 6, wherein the Lewis acid is one of an organic Lewis acid and an inorganic Lewis acid.

9. An electrochemical cell, comprising:
a non-aqueous solvent; and
an organic metal salt, comprising a structure represented by formula I (I)

wherein
M is lithium;
Z is a Lewis acid; and
Y is one selected from a group consisting of an alkyl group, a sulfoalkyl group, a carboalkyl group, a nitroalkyl group, a nitro group, an aldehyde group, a carboxyl group, $OCF_3$, $OCH_2CF_3$, $OCF_2CF_3$ and $OCF_2CF_2CF_3$.

10. An electrochemical cell as claimed in claim 9, being one of a primary and a secondary rechargeable cell.

11. An electrochemical cell as claimed in claim 9, wherein the non-aqueous solvent and the organic metal salt form a non-aqueous electrolyte of the electrochemical cell.

12. An electrochemical cell as claimed in claim 9, wherein the Lewis acid is one selected from a group consisting of $BX_3$, $AlX_3$ and $PX_5$, wherein X is a halogen.

13. An electrochemical cell as claimed in claim 9, wherein the Lewis acid is one selected from a group consisting of $BF_3$, $BCl_3$, $BBr_3$, $AlF_3$, $AlCl_3$, $PF_5$, $PCl_5$, $B(OCH_3)_3$, $B(OCF_3)_3$, $B(C_6F_5)_3$, $B(OCH(CF_3)_2)_3$, $B(OC_6F_5)_3$, $B(CF_3)_3$, $B(CF_2CF_3)_3$, $B(OC_6H_4F)_3$, $B(OC_6H_3F_2)_3$, $B(OC_6H_2F_3)_3$, $B(OC_6HF_4)_3$, $B(OCH_2CF_3)_3$, $B(OCH_2C_3F_7)_3$ and $B(CO(CH_3)(CF_3)_2)_3$.

14. An electrochemical cell as claimed in claim 9, wherein the alkyl group is one selected from a group consisting of $CH_3$, $C_2H_5$ and $C_3H_7$.

15. An electrochemical cell as claimed in claim 9, wherein the non-aqueous solvent is an alkyl carbonate.

16. An electrochemical cell as claimed in claim 15, wherein the alkyl carbonate is one selected from a group consisting of ethylene carbonate (EC), dimethyl carbonate (DMC), diethyl carbonate (DEC), ethyl methyl carbonate (EMC) and propylene carbonate (PC).

\* \* \* \* \*